United States Patent [19]
Thorne

[11] Patent Number: 5,957,892
[45] Date of Patent: Sep. 28, 1999

[54] SAFETY CATHETER INSERTION APPARATUS AND METHODS

[75] Inventor: David L. Thorne, Kaysville, Utah

[73] Assignee: Specialized Health Products, Inc., Bountiful, Utah

[21] Appl. No.: 09/041,553

[22] Filed: Mar. 12, 1998

[51] Int. Cl.[6] .................................................. A61M 5/32
[52] U.S. Cl. ........................ 604/162; 604/192; 604/263
[58] Field of Search ................................ 604/110, 192, 604/197, 198, 263, 162, 164, 167

[56] References Cited

U.S. PATENT DOCUMENTS

| | | | |
|---|---|---|---|
| 4,762,516 | 8/1988 | Luther | 604/164 |
| 4,790,828 | 12/1988 | Dombrowski et al. | 604/198 |
| 4,832,696 | 5/1989 | Luther | 604/164 |
| 4,911,694 | 3/1990 | Dolan | 604/198 |
| 4,935,013 | 6/1990 | Haber et al. | 604/192 |
| 5,139,489 | 8/1992 | Hollister | 604/192 |
| 5,147,303 | 9/1992 | Martin | 604/110 |
| 5,154,285 | 10/1992 | Hollister | 206/365 |
| 5,176,655 | 1/1993 | McCormick et al. | 604/192 |
| 5,193,552 | 3/1993 | Columbus et al. | 128/760 |
| 5,232,455 | 8/1993 | Hollister | 604/110 |
| 5,246,427 | 9/1993 | Sturman et al. | 604/192 |
| 5,246,428 | 9/1993 | Falknor | 604/198 |
| 5,254,099 | 10/1993 | Kuracina et al. | 604/198 |
| 5,256,153 | 10/1993 | Hake | 604/198 |
| 5,356,392 | 10/1994 | Firth et al. | 604/198 |
| 5,403,283 | 4/1995 | Luther | 604/164 |
| 5,447,501 | 9/1995 | Karlsson | 604/198 |
| 5,480,385 | 1/1996 | Thorne et al. | 604/110 |
| 5,487,734 | 1/1996 | Thorne et al. | 604/195 |
| 5,520,654 | 5/1996 | Wahlberg | 604/164 |
| 5,542,927 | 8/1996 | Thorne et al. | 604/110 |
| 5,549,708 | 8/1996 | Thorne et al. | 604/110 |
| 5,573,510 | 11/1996 | Isaacson | 604/158 |
| 5,690,619 | 11/1997 | Erskine | 604/263 |
| 5,695,474 | 12/1997 | Daugherty | 604/263 |
| 5,746,726 | 5/1998 | Sweeney et al. | 604/192 |
| 5,814,018 | 9/1998 | Elson et al. | 604/110 |
| 5,823,997 | 10/1998 | Thorne | 604/110 |

*Primary Examiner*—Wynn Wood Coggins
*Assistant Examiner*—Sharon Finkel
*Attorney, Agent, or Firm*—Gale H. Thorne

[57] ABSTRACT

Parts integrally associated with a shortened I.V. insertion needle handle to provide, in as few as one molded part, an extendable safety guard for a catheter insertion needle and its sharpened tip. The safety guard comprises a plurality of rigid segments serially connected by a plurality of living hinges. The segments are disposed about the insertion needle, folded upon each other during the medical procedure and extended at the end of the procedure to form a secure, substantially fixed length safety sheath which conforms to the long axis of the needle. During the procedure, the safety guard is folded and conveniently disposed about a proximal portion of the needle. At the end of the procedure, the safety guard is extended by a relatively short motion associated with an arc distance of a proximal segment of the enclosure to protectively guard and secure the needle. The needle becomes a part of a structure which is cooperatively formed by both needle and enclosure. The resulting structure has a fixed, predetermined length and protects from inadvertent exposure to the needle tip.

11 Claims, 8 Drawing Sheets

SAFETY CATHETER INSERTION APPARATUS AND METHODS

FIELD OF INVENTION

This invention relates generally to safety devices for hollow bore medical needles and particularly to medical catheter and other hollow needle products which comprise protective needle sheaths for securely shielding sharp medical needle tips after being withdrawn from a patient. This invention more particularly relates to sheaths which are extended to a locked, needle-tip safeguarding position after the needle is withdrawn from the catheter.

PRIOR ART

Problems associated with inadvertent needle sticks are well known in the art of blood sampling, percutaneous medication injection, catheter insertion and other medical procedures involving uses of medical needles. Ever increasing attention is being paid to needle stick problems due to the contemporary likelihood of being exposed to AIDS and Hepatitis.

Commonly, procedures involving removing a needle from a patient require a technician to use one hand to place pressure at the catheter insertion site from which the needle is being withdrawn while removing the needle apparatus with the other hand. It is common practice for a tending technician to give higher priority to care for problems associated with an open catheter lumen than is given to disposal of a needle. In the case of commonly used, non-safety devices such priority either requires convenience of an available sharps container within ready reach or another means for safe disposal without leaving the patient's side. Providing adequate care is often compounded by patient condition and mental state (e.g. in burn units and psychiatric wards). Under such conditions, it is often difficult, if not impossible, to take appropriate procedures to properly dispose of a used, exposed needle while caring for a patient.

Widespread knowledge and history associated with needle care and disposal problems have resulted in conception and disclosure of a large number of devices, each of which represents an attempt to provide not only a solution to the problem of needle sticks but also a device which is commercially viable (i.e. cost and price competitive with currently used non-safety devices).

Examples of disclosures of safety devices which protect needles by moving a protective shield over a sharp end of a syringe or other hollow bore medical needle are found in U.S. Pat. No. 4,832,696, issued May 23, 1989 to Ronald B. Luther, et al. (Luther), U.S. Pat. No. 5,348,544, issued Sep. 20, 1994 to Sweeney et al. (Sweeney), U.S. Pat. No. 5,246,428 issued Sep. 21, 1993 to Donald W. Falknor (Falknor), U.S. Pat. No. 5,256,153 issued Oct. 26, 1993 to Lawrence W. Hake (Hake) and U.S. Pat. Nos. 5,139,489 and 5,154,285, issued Aug. 18, 1992 and Oct. 13, 1992, respectively, to William H. Hollister (Hollister). There are many other examples of safety devices which retract needles into housings, however, this instant invention is more directly related to devices which extend a shield over a needle rather than to those which employ needle retraction.

An I.V. Catheter Safety System, marketed under the trademark PROTECTIV Plus by Johnson & Johnson Medical, Inc., is a product based upon Luther and other unidentified patents pending. This catheter safety system comprises an elongated housing to which is attached an insertion needle and a needle guard which is slidably mounted within the housing. The needle guard is adapted to be moved forward relative to the housing to a safety position over the needle (or, conversely to have the needle and housing retracted until the needle resides within the safety position). Once the needle guard is moved fully forward (or the housing and needle are fully retracted), the guard and housing become permanently locked and so disposed in a needle protecting state. Once the guard and housing are locked, the needle is fully encased for safe disposal. Though proved safe in concept and operation, the process of moving the guard forward (or retracting the needle and housing) is not easily performed, especially for care givers with small hands or for long needles or both. It is common for two handed operation to be required of a care giver to move the needle into the safety of the guard.

Sweeney discloses a device comprising a guard which is manually, slidably movable along a needle canula from a position proximal to a user to a distal position where the needle tip is shielded. The device comprises a hinged arm which extends away from the needle canula and which is moved distally to collapse upon itself to extend the shield over the tip. Access to the tip is denied by a metallic clip. An alternative embodiment is also disclosed by which the manual operation is augmented by a spring. A device based upon Sweeney is currently being distributed by Becton Dickinson and Company, Franklin Lakes, N.J. in which three separate parts (two injection molded and one metal clip) are used to mechanize the guard. Once the device is extended to shield a needle tip, it cannot be easily reset to recover use of the needle for a subsequent procedure. Also, the hinged arm requires activation in the region of the needle itself and comprises parts which are of a size which occasionally impedes a user's line of sight to insertion locations.

Falkner, and related disclosures, disclose devices comprising shields which are automatically releasible to extend distally from a user to cover a needle. The devices comprise latch mechanisms which are manually switched between unlatched and latched positions to free the needle for use and lock the shield over the needle, respectively. Of course, position of the latch mechanism provides a visual interpretation of the safety of the device (i.e. whether or not a latch is engaged), but that is the only safety mechanism and a "missed" indicator of latch mechanism position may be possible in stressful circumstances. When the latch mechanism is in the unlatched position, access to the needle is not only possible, but likely, when the front of the device is impacted by a body part. In addition, the shield, though made of transparent material, covers a portion of an attached syringe body until fully extended and may make portions of volume measurement indicia on the syringe body difficult to read with accuracy when the syringe is being used in a titrating application.

Hake is representative of disclosure of devices comprising a manually slidable guard which is disposed over a syringe body during a medical procedure involving a medical syringe needle and manually, slidably moved distally into a needle guarding position usually at the end of the procedure. Commonly users of such devices complain of difficulty of seeing measurement indicia while the guard is disposed over the syringe body and of danger of inadvertent needle sticks while sliding the guard distally to cover the needle. As well, it is generally difficult to determine whether a guard is in a locked or unlocked state when it covers the needle, making an additional possibility of inadvertent needle stick.

Hollister discloses a needle protection device which may be used with a double-ended needle assembly or with a simpler single needle system. The protection device comprises a substantially rigid housing flexibly connected to a container (for a vacuum tube sampling system) or to a needle hub. To exercise the protection device, the rigid member is pivotally rotated into engagement with an exposed needle of the double-ended needle assembly and is securely affixed to the exposed needle. A major drawback of the needle protection device of Hollister is the size and position of the rigid housing. During use of an assembly or system in a medical procedure, length and position of the housing member is considered by some to be inconvenient. A second drawback is the requirement either for two handed operation to pivot the housing to engage the needle or for the requirement to find and use a stable support surface against which the housing is pressed while the needle is swung into engagement with the housing. In a currently marketed format, an integral container holder version of the device disclosed by Hollister comprises two injection molded parts which permit the housing to be rotated, as much as possible, out of the way during a medical procedure. Such a format requires five injection molded parts, including a disposable needle assembly.

Generally, other than acceptance of the type of operation offered by such devices, commercial viability is dependent upon manufacturing cost. Purchasing decisions in the area in which these devices are used are very cost sensitive. If gains in either improvement in safety or in labor savings are not found to make a device sufficiently competitive with contemporary competitive items, those devices are usually not found to be commercially viable. Motivation for providing a cost competitive self-retracting needle apparatus coupled with improved safety of use of the apparatus is the basis for conception and reduction to practice of the instant inventions disclosed herein.

BRIEF SUMMARY AND OBJECTS OF THE INVENTION

In brief summary, the novel invention disclosed herein dramatically diminishes known major problems resulting from injury-related needle sticks which occur when needle tips are bared as a medical needle is withdrawn from a patient at the end of a catheter insertion procedure, but, perhaps more important to general patient welfare, this invention provides opportunity for fabrication of a very low cost safety catheter insertion needle system. Low cost is achieved by a dramatic reduction in injection molded parts whereby an extendable needle covering safety sheath is integrally molded with other parts such as a hub for the needle and a handle segment for the catheter insertion device. For remarkable ease of use, this device employs apparatus which augments and thereby reduces distance required to accomplish extension (actuation) of the sheath (i.e., as an example, the range of finger motion relative to the distance required to lengthen the sheath). This limiting of required motion significantly reduces the degree of difficulty in actuating the safety sheath, especially when compared against motion required to activate other devices, such as those based upon Luther.

Generally, basis for this novel invention is a foldable sheath which is initially folded proximally about a medical needle to permit access to the needle and an associated catheter in a medical procedure. The sheath is hingeably attached to structure (e.g. a needle hub and handle segment) at a point away from a sharpened needle tip which is the object of subsequent enclosure to protect a user from inadvertent needle stick. At the end of the procedure, the sheath is facilely unfolded and thereby extended along and about the long axis of the needle to fully capture the needle and its tip. The sheath comprises a slidable hub in the form of a hollow cylinder or other needle encircling element which forms a connection with a proximal segment of the catheter. As the sheath is extended, it urges the catheter distally until the catheter is separated from the needle. At this point, the sharpened tip is totally enclosed within the cylinder portion of the sheath. When the sheath is fully extended, it forms a sandwich about the needle and is latched such that the sheath and needle combine to form an integral structure. The structure formed thereby is a substantially incontractible member which may conformably bend as the needle bends but which maintains a safe guarding enclosure about the needle tip. To permit the sheath to unfold along and about the needle, each folded part of the sheath is serially constructed of a plurality of rigid segments. At least two segments comprise an orifice through which the needle passes and about which the segments rotate while the sheath is being extended. Each segment is connected to at least one other segment by a hinge, which is preferably a molded, living hinge, and comprises a channel into which the needle nests when the sheath is fully extended. At least one of the segments comprises a catch which secures the sheath about the needle when the sheath is in the extended state. It is important to note that the sheath is extended by a movement which involves only one segment of the sheath and, thus, the sheath is fully extended by a motion which is far shorter than the length of full extension of the sheath. Such a restriction in required motion is very important when considering difficulty of extending long sheaths or shrouds of other devices.

Accordingly, it is a primary object to provide a manually actuated safety sheath for an I.V. catheter needle which is a single molded part.

It is another object to provide a safety sheath which is integrally molded with another part of a catheter insertion device.

It is an important object to provide an integral, self-contained, safety I.V. catheter insertion device comprising a housing, an insertion needle hub, and a safety sheath, the entire system being formed as one injection molded part.

It is an object of chief importance to provide a sheath which is extended by a range of motion which is but a fraction of the extended length of the sheath.

It is an object to provide a safety sheath which is an adequate safeguard for a catheter insertion needle without resorting to use of an added barrier part, such as a metal clip.

These and other objects and features of the present invention will be apparent from the detailed description taken with reference to accompanying drawings.

DETAILED DESCRIPTION OF THE ILLUSTRATED EMBODIMENTS

In this description, unless a specific object is referenced, the term proximal is used to indicate that segment of a device which is normally closest to a user (e.g. a clinician or technician who is treating a patient). In like manner, the term distal refers to the other (away from the user) end. Reference is now made to the embodiments illustrated in FIGS. 1–8 wherein like numerals are used to designate like parts throughout.

Figure 1:
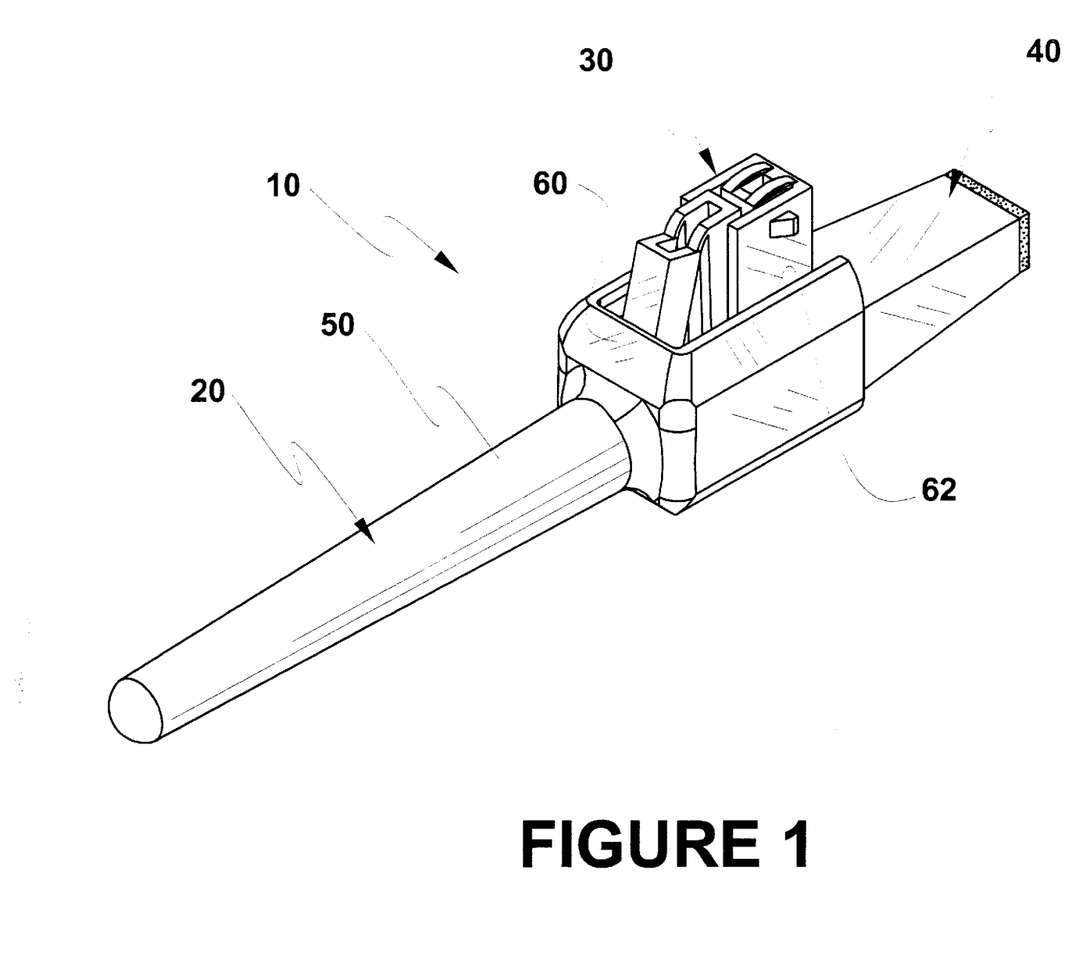
FIG. 1 is a perspective of a completely assembled safety catheter insertion device in accordance with the instant invention disclosed herein.

Reference is now made to FIG. 1 wherein an assembled catheter insertion device 10 is seen to comprise a removable protective needle cover 20, a folded safety sheath 30, and a handle 40. It is common practice to maintain catheter insertion devices in hermetically sealed packages (often called bubble packs) to preserve a presterilized condition prior to use. As such packages are well known in the medical device art, no such packaging is dealt with further herein.

Needle cover 20 comprises a distally disposed elongated hollow barrel portion 50 and more proximally disposed handle attachment section 60. Section 60 further comprises a "U" shaped slot 62 wherethrough sheath 30 rises.

Figure 2:
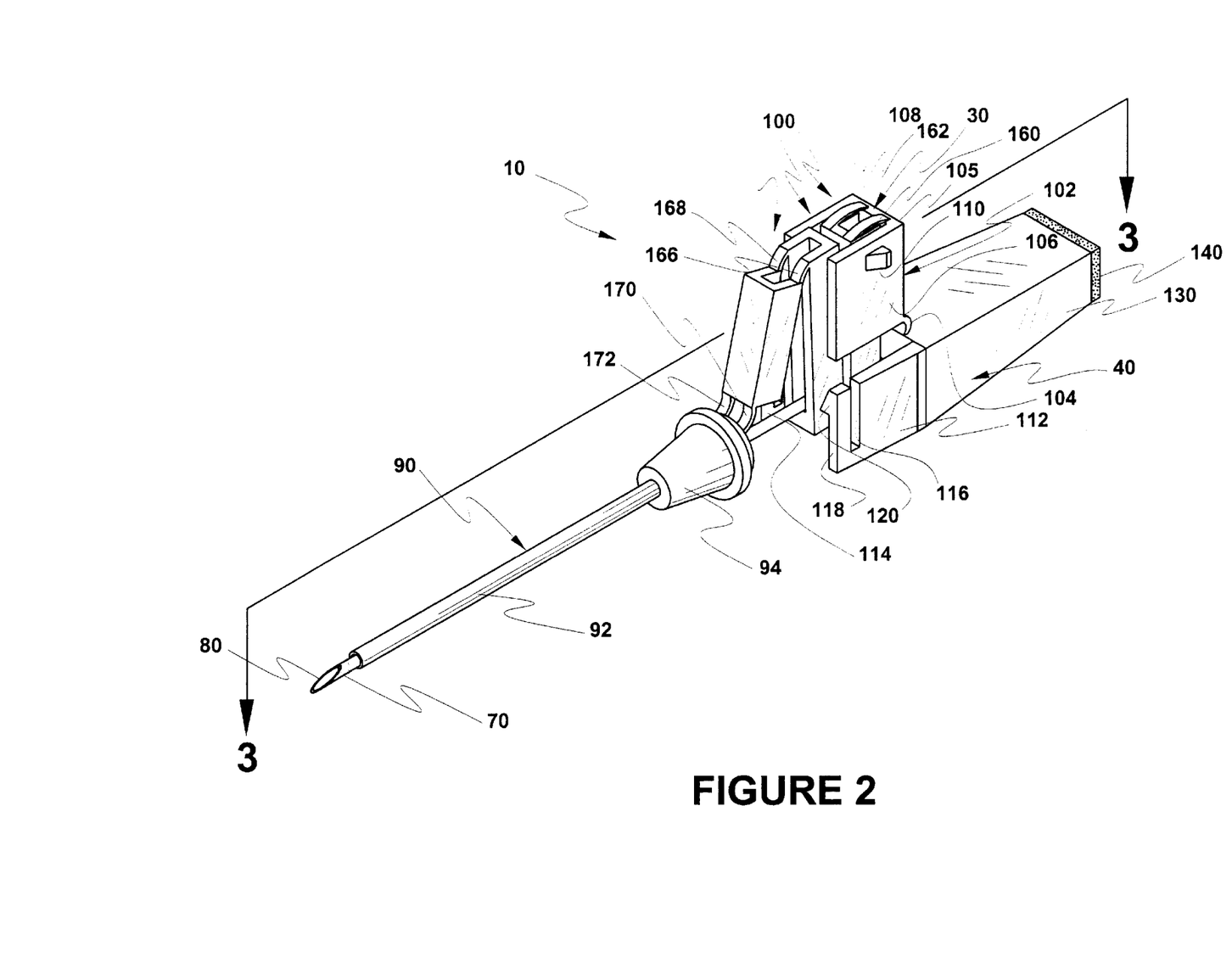
FIG. 2 is a perspective of the device seen in FIG. 1, with a protective needle cover removed.

Device 10, with cover 20 removed, in preparation for use is seen in FIG. 2. With cover 20 removed, device 10 is seen to comprise a catheter insertion needle 70 and associated sharp needle tip 80 and a catheter 90 disposed over needle 70 and removably affixed to sheath 30. Catheter 90 comprises an elongated hollow tubular portion 92 snugly fitted about needle 70 and a proximally disposed connector 94, generally formed as a Luer fitting.

Protective sheath 30 comprises a plurality of substantially rigid (and substantially incompressible) segments (generally numbered 100). Each segment 100 is hingeably interconnected with at least one other segment 100 such that unfolding segments 100 elongates sheath 30 distally along needle 70. A most proximal segment 102 of sheath 30 is hingeably affixed to handle 40 through hinge 104. Segment 102 is a "U" shaped part having a faceplate 105, proximally disposed when sheath 30 is in a folded state. Extending distally from proximally disposed faceplate 105 are a pair of juxtaposed side plates 106 and 108. Each side plate 106 and 108 comprises a protruding latch. (Only protruding latch 110 is seen on side plate 106 in FIG. 2; however, a complementary latch is disposed on side plate 108.)

As sheath 30 is compactly folded and does not require a proximally disposed elongated section of a needle shield (e.g. such elongated needle shields which were earlier disclosed in cited related art) for use in protectively shielding needle 70 and needle tip 80, handle 40 is compact and resembles handles of contemporary commercially available non-safety catheter insertion devices. Such devices often remain devices of choice of caregivers due to ease of handling more compact handles. Handle 40 comprises a pair of distally projecting juxtaposed guards 112 and 114. Note that guard 112 comprises a slot 116 which relieves a segment 118 from the rest of guard 112 and allows segment 118 to flex. Segment 118 further comprises a catch 120. Thus, as segment 102 is rotated about hinge 104 forcing latch 110 upon catch 120, segment 118 flexes outward permitting latch 110 to be displaced past catch 120 whereupon segment 118 flexes inward causing latch 110 to be securely locked in place by catch 120. In similar fashion, a catch 122 is affixed to a flexible segment 124 associated with a slot 126 (seen only in FIG. 8) in guard 114 to provide a redundant locking capability.

Handle 40 further comprises a portion 130 which is ergonomically shaped to be facilely grasped when device 10 is used to insert a catheter and when segment 102 is rotated to extend sheath 30. Proximally affixed to handle 40 is a backplate 140 made of a material which is permissive to flow of gasses, yet impermeable to flow of liquids. Such materials are well known in the art and in common use in contemporary catheter insertion devices and will not be further characterized therefore herein.

Figure 3:
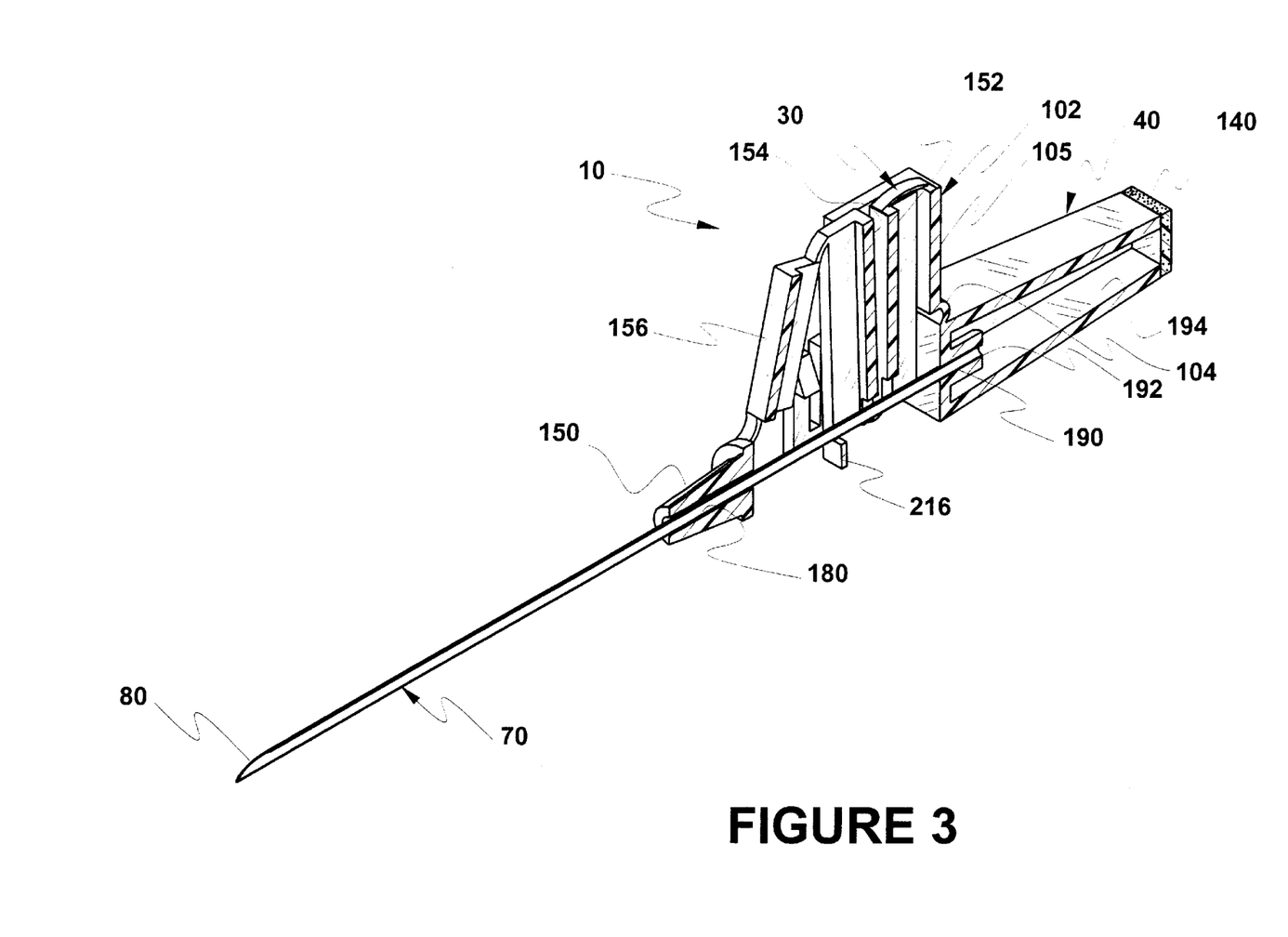
FIG. 3 is a section taken along lines 3—3 of FIG. 2, after removal of a catheter seen covering a medical needle in FIG. 2.

Additional details of device 10, with sheath 30 folded, are seen in FIG. 3. Catheter 90 is removed from device 10 to permit clear presentation of needle 70 and a distal segment 150 of sheath 30. Though more (or fewer) numbers of segments may be used within the scope of the instant invention disclosed herein, in the embodiment seen in FIGS. 1–8, sheath 30 comprises proximally to distally disposed segments 102, 152, 154, 156 and 150, respectively.

Figure 4:
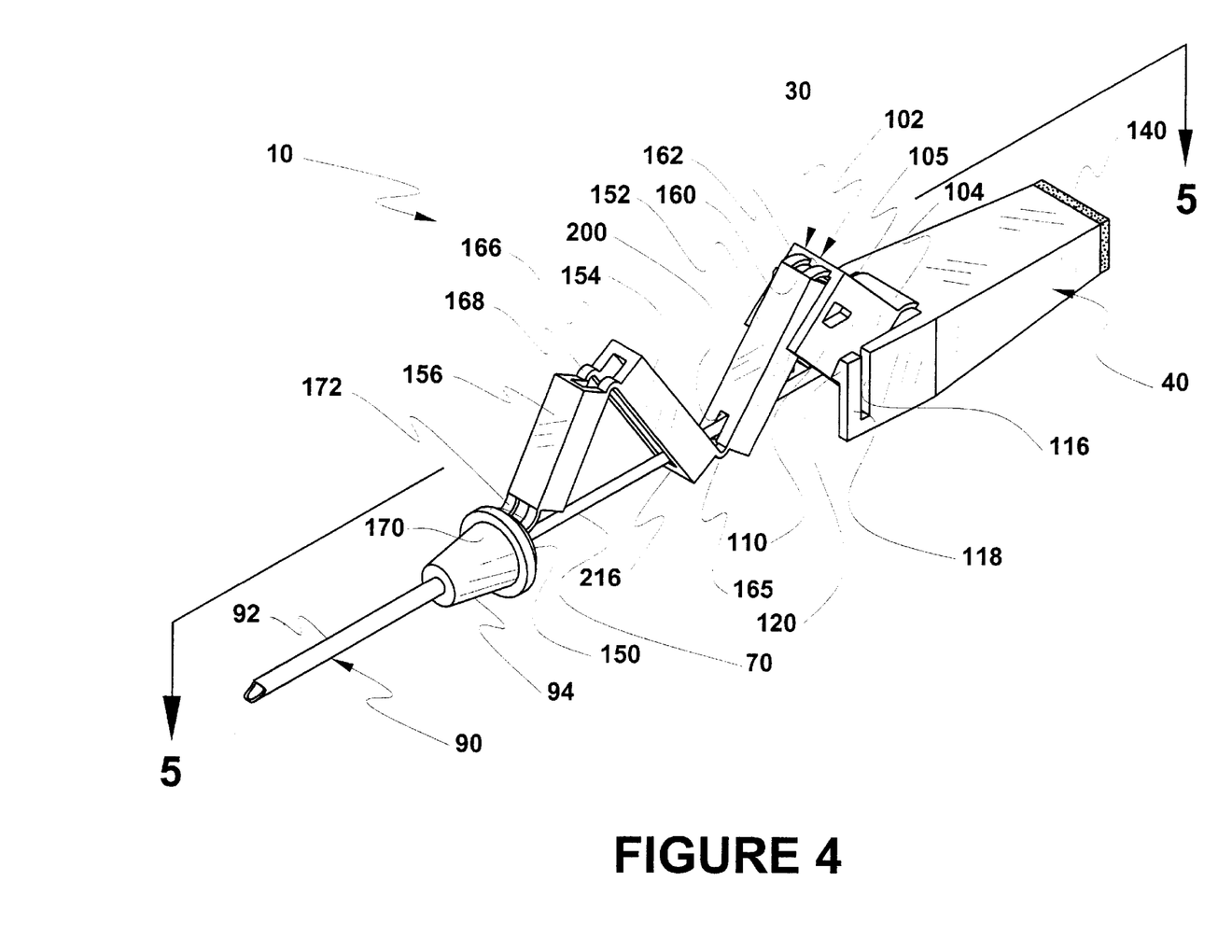
FIG. 4 is a perspective of the device as seen in FIG. 2, with a safety sheath partially extended to displace the catheter distally along the long axis of the medical needle.
Figure 6:
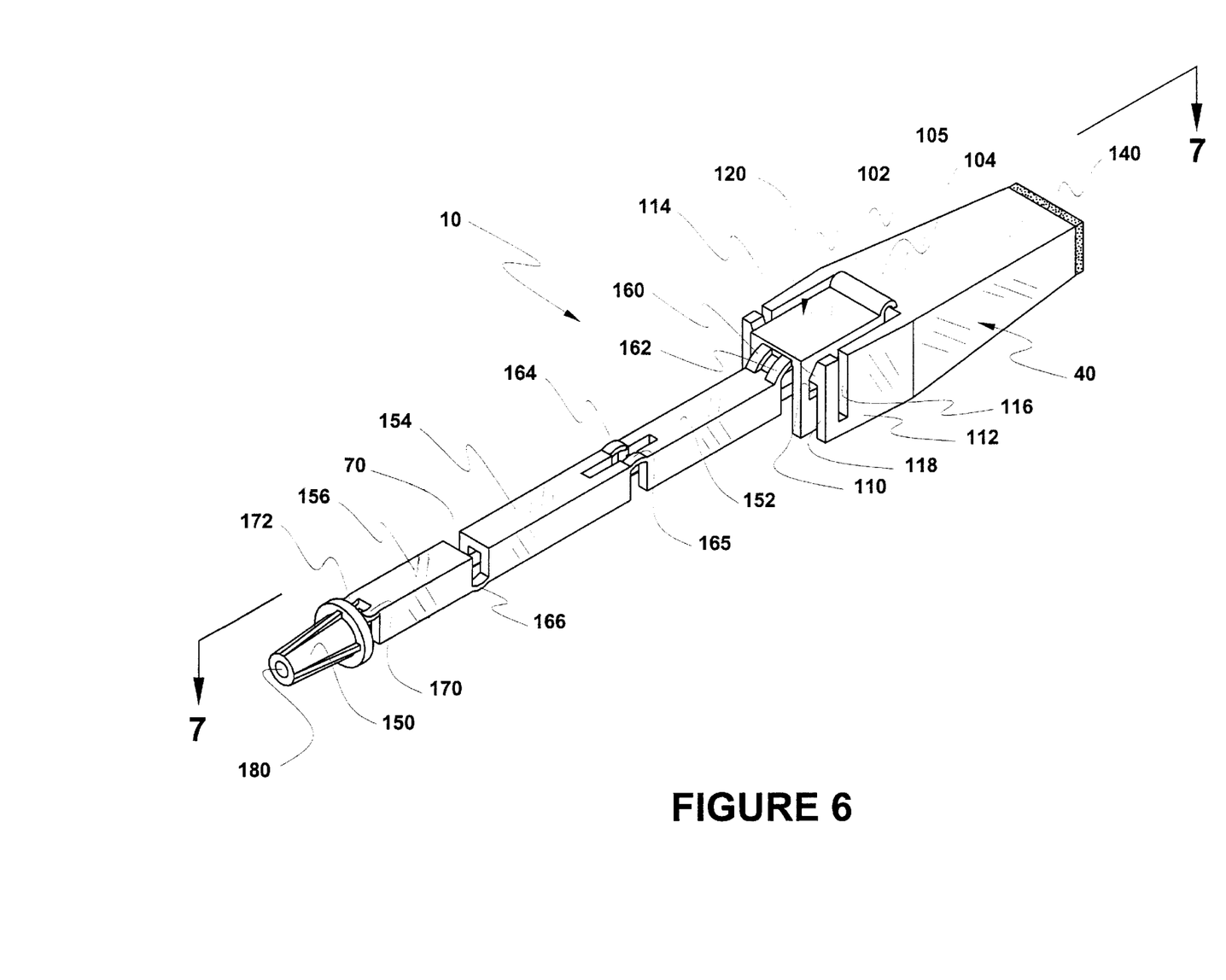
FIG. 6 is a perspective of the device seen in FIG. 4, with the sheath fully extended into a needle safeguarding state and the catheter removed.

Reference is made to FIG. 4 for a clearer presentation of interconnections between segments of sheath 30. Each segment, 102, 152, 154 and 156, comprises a generally "U" shaped channel which sheathes and protects needle 70 and needle tip 80 when sheath 30 is unfolded and extended. As earlier cited, segment 102 is hingeably affixed to handle 40 by hinge 104. Segment 102 is similarly affixed to segment 152 by a pair of hinge parts 160 and 162. Segment 152 is likewise affixed to segment 154 by hinges 164 and 165. In similar manner, segment 154 is affixed to segment 156 by a pair of hinges 166 and 168. Finally, segment 156 is hingeably affixed to segment 150 by a pair of hinges 170 and 172. Note that hinges 160, 162, 164, 165, 166, 168, 170 and 172 are paired hinges. Such pairing permits those hinges to not interfere with needle 70, when sheath 30 is unfolded and extended as seen in FIG. 6.

Reference is again made to FIG. 3 wherein a pathway for needle 70 is clearly seen. As part of the needle pathway, segment 150 comprises a bore hole 180 disposed along the long axis of needle 70 and sized large enough to permit facile displacement of segment 150 along needle 70 but small enough to limit undue transverse displacement of segment 150 relative to needle 70. Proximally, handle 40 comprises a bore hole 190 into which a proximal end 192 of needle 70 is disposed and securely affixed. Methods for affixing a hollow bore medical needle, such as needle 70, into such a bore hole as hole 190 are well known in the art of manufacturing medical needle devices and will not be further treated herein. Handle 40 also comprises a cavity 194 proximal to hole 190. In combination with backplate 140, cavity 194 provides a flash chamber for blood cursing through needle 70 as a result of entry of tip 80 into a blood vessel of a patient. Of course, handle 40 must be at least translucent if cavity 194 is to be used as a flash chamber.

Figure 5:
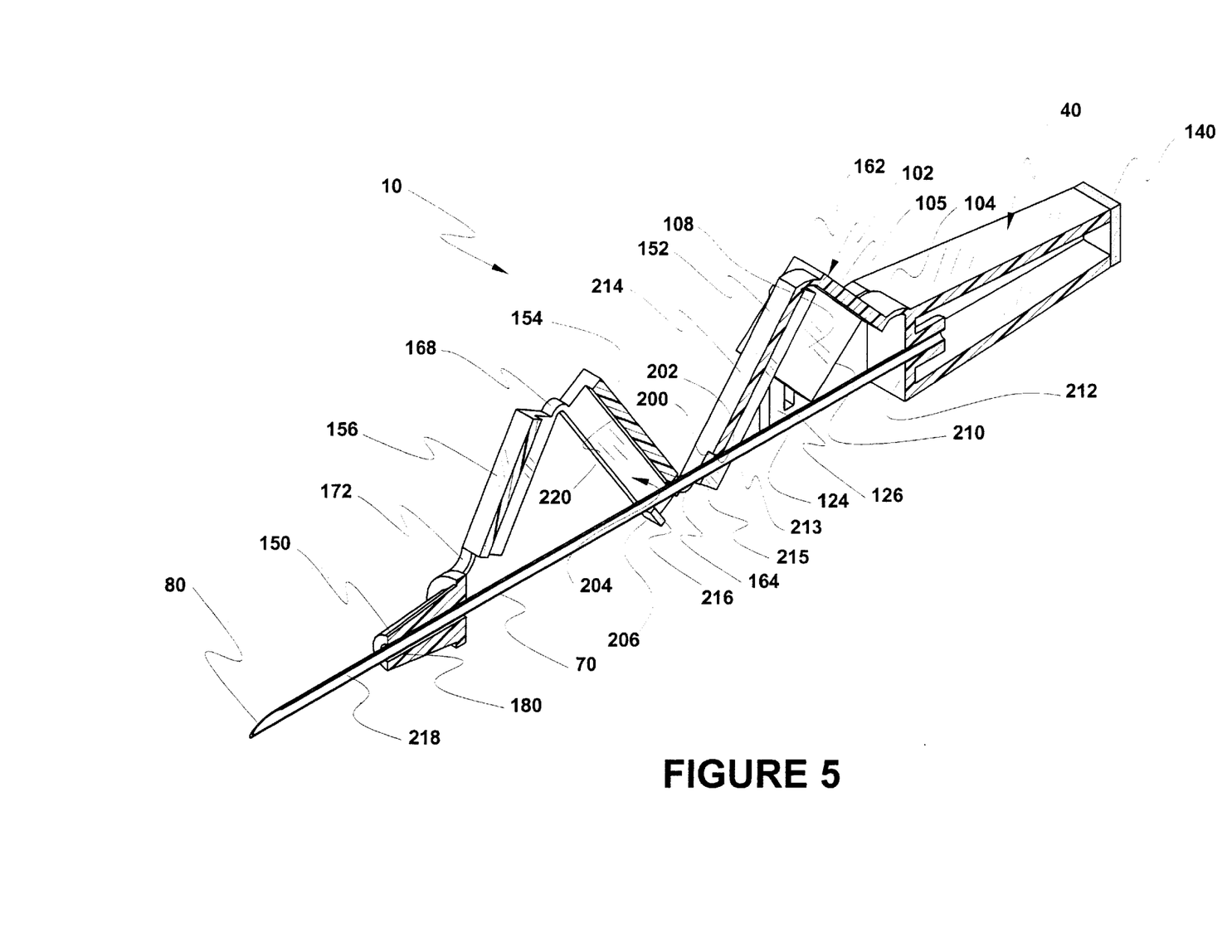
FIG. 5 is a section taken along lines 5—5 of FIG. 4, with the catheter having been removed.

As earlier disclosed, sheath 30 is disposed in a folded state when catheter 90 is inserted with the aid of needle 70 into a patient. Once the catheter insertion is accomplished, catheter 90 may be displaced from needle 70 by rotating segment 102 as seen in FIG. 4. By forcing faceplate 105 to rotate distally, such as with a forefinger of a hand while holding handle 40 with the same hand, sheath 30 is extended. Note the amplification of distance catheter 90 is moved by segment 150 relative to distance required to move segment 102. This amplification facilitates displacement of catheter 90 along needle 70. Rotation of segment 102 about hinge 104 thrusts segment 152, through hinges 160 and 162 inferiorly toward needle 70. Segment 152 comprises an inferiorly disposed slot 200 (see FIG. 5) proximal to needle 70. Slot 200 comprises a superiorly disposed ledge 202, as best seen in FIG. 5. Inferior displacement of segment 152 forces ledge 202 against needle 70, first, urging segment 152 distally and, second, levering segment 154 superiorly through hinge 164.

Segment 154 comprises a rectangular slot 204 wherethrough needle 70 is disposed. Segment 154 further comprises a ledge 206 which bounds slot 204 on an inferior side of needle 70. As segment 154 is levered superiorly, ledge 206 is displaced to contact needle 70 thereby causing segment 154 to rotate causing hinge 168 (and hinge 166) to be displaced distally and inferiorly. The displacement of hinge 168 (and hinge 166) is communicated from segment 154 to segment 156.

Inferior displacement of hinge 168 (and hinge 166) rotates segment 156 inferiorly while communicating through hinge 172 (and hinge 170) to displace segment 150 distally along needle 150. As a consequence, catheter 90 is distally displaced thereby withdrawing needle 70 from catheter 90 by facile rotation of faceplate 105. Once needle 70 and catheter 90 are disjoined, catheter 90 may be disconnected from segment 150 and used in medical procedures sans device 10.

Figure 7:
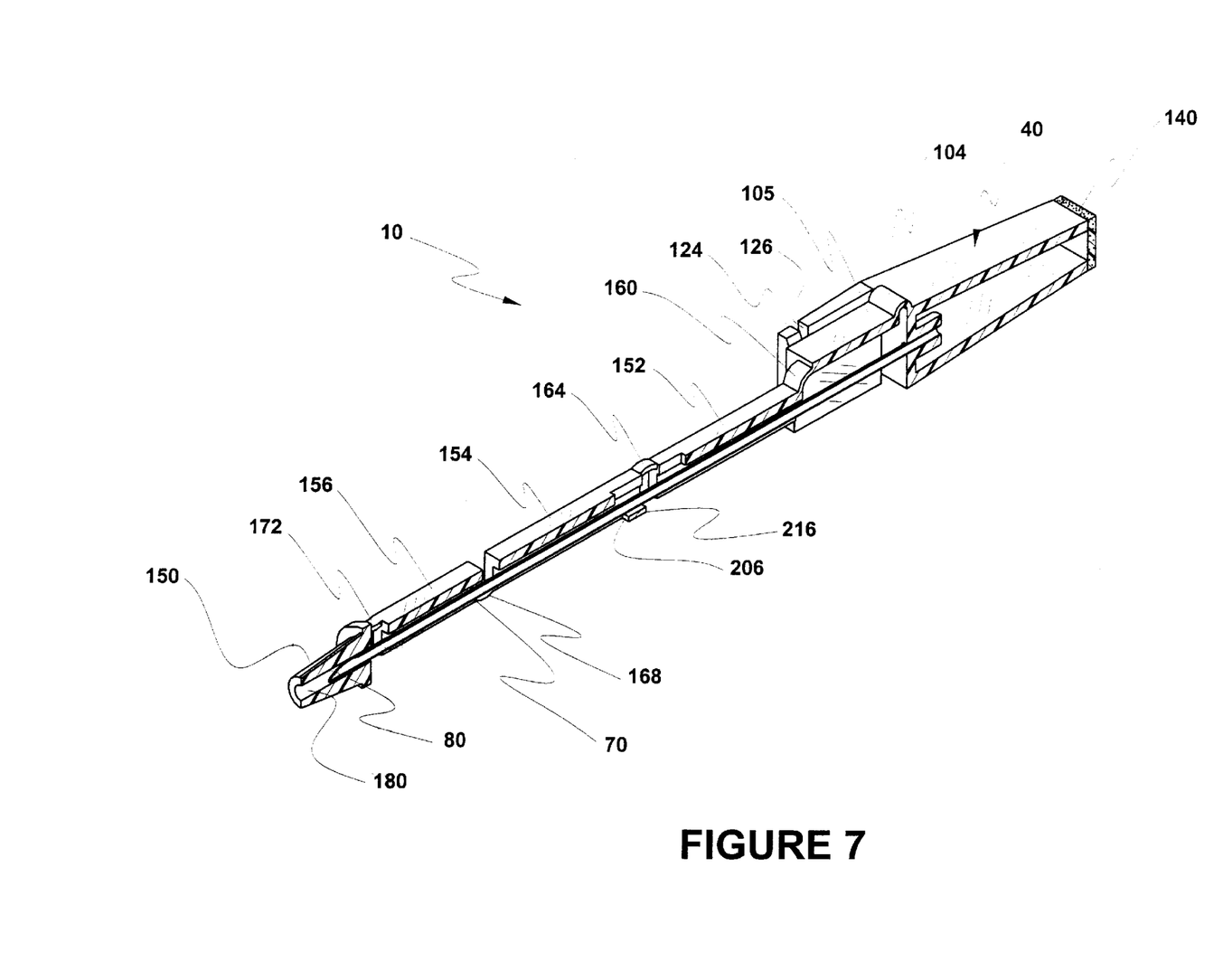
FIG. 7 is a section taken along lines 7—7 of FIG. 6.

As a consequence of fully extending sheath 30, as seen in FIGS. 6 and 7, needle tip 80 is captured and fully enclosed in segment 150. The complementary full rotation of segment 102 causes at least one latch, and preferably both latches (latch 110 and the latch associated with side plate 108, but unnumbered due to not being seen in the Figures), to be locked against catches 120 and 122. When at least one latch is affixed against a catch, needle 70 and sheath 30 combine to form a safety structure which surrounds and securely maintains needle tip 80 within a protective shield.

In order to understand the way the safety structure is achieved, one should consider the geometry defined by the combination of needle 70 and sheath 30 as sheath 30 extends to a planar state. Referring again to FIG. 5, segment 102 comprises at least one inferiorly disposed surface 210 which engages against a distal surface 212 of handle 40 when segment 102 is rotated into the safety state. Note that a variable length portion 213 of needle 70 is disposed under segments 102 and a proximal portion 214 of segment 152 during rotation, portion 213 being of fixed length when segment 102 is fully rotated.

When ledges 202 and 206 are disposed to be in contact with needle 70, a triangular structure is formed among a portion 215 of segment 152 which is distal to ledge 202, a portion 216 of segment 154 which is proximal to ledge 206, hinge 164 (and hinge 165) and that variable portion 218 of needle 70 which lies between ledges 202 and 206. Another substantially triangular structure is formed by that portion 220 of segment 154 which is distal to ledge 206, segment 156, hinge 172 (and hinge 170) and hinge 168 (and hinge 166). Further, angles formed by intersection of segment 152 and needle 70 (i.e. angles 214/202/70 and 215/202/70) are effectively opposing angles of two straight lines and are therefore equal to each other in magnitude. In the same manner, angles formed by intersection of segment 154 and needle 70 (i.e. angles 216/206/70 and 220/206/70) are effectively opposing angles of two straight lines and are also equal to each other in magnitude.

Structure of segment 102 and hinges 104 and 162 (hinge 160) are designed to cause segment 152 to be disposed against needle 70 when segment 102 is fully rotated, as seen in FIGS. 6 and 7. So disposed angle 216/206/70 is 0°, and consequently, so is angle 215/202/70. Since angle 215/202/70 is a base angle of the triangle formed by portions 215, 216 and 218, angle 216/206/70 is forced to 0° and, consequently, so is angle 220/206/70. A consequence zeroing of angle 220/206/70 results in complete extension of both segments 154 and 156. Thus, when segment 102 is fully rotated, all segments 152, 154 and 156 are also fully rotated to be disposed in alignment with needle 70 and substantially affixed thereto as a single structure. In this manner, needle tip 80, is fully enclosed by segment 150 and no segment 152, 154 or 156 is free to be angularly displaced away from needle 70, resulting in a safety structure which is substantially incompressible and conveniently disposed about needle 70.

In the design of sheath 30, care should be taken to prevent binding of segments of sheath 30 and subsequent impeding of sheath 30 extension as faceplate 105 is rotated. Note that, as long as needle 70 and two hinged segments form an open triangle, no binding caused by the needle and those two hinged segments can occur. It is appropriate, therefore, to add structure to any segment of sheath 30 which may be party to binding to provide a physical bias which eliminates any possibility of binding of one segment relative to another segment.

Figure 8:
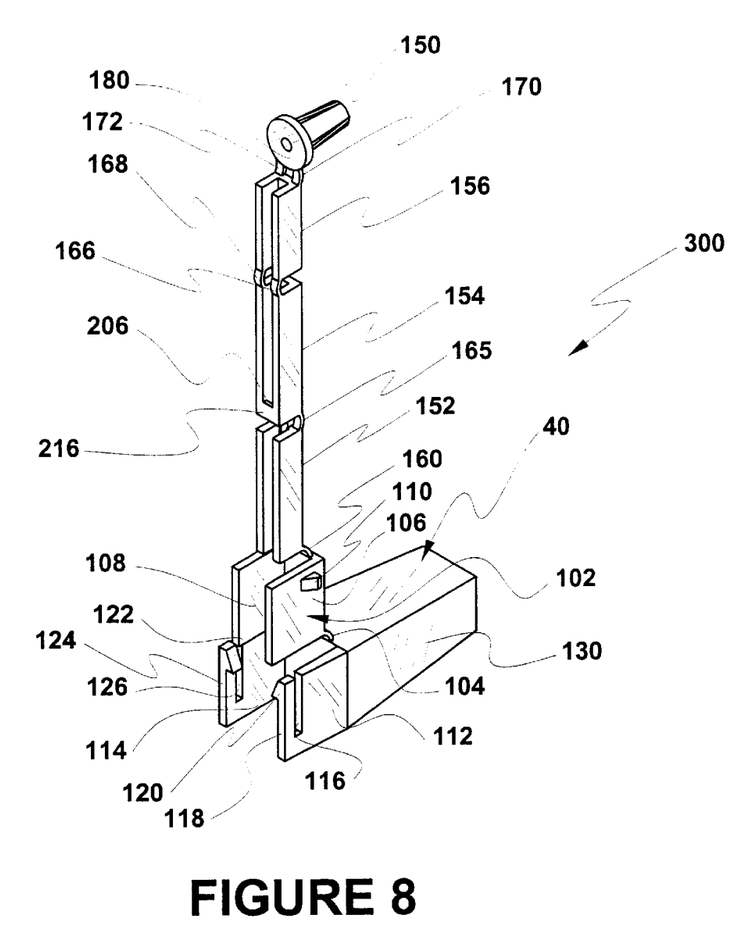
FIG. 8 is an as molded part comprising the sheath, including a catheter hub, and a device handle.

Reference is now made to FIG. 8 wherein a single molded part 300 from which device 10 may be constructed is seen. As mentioned earlier, cost must be considered as a primary factor which must be considered basic to commercial acceptance of safety catheter insertion devices. That cost comprises cost to mold and cost to assemble. For this reason, it is preferred to mold as much of device 10 as a single molded part as possible. Note that part 300 is easily formed as an integral molded part which includes handle 40 and sheath 30 comprising segments 102, 152, 154, 156 and 150 and hinges 104, 160, 162, 164, 165, 166, 168, 170 and 172. Note further that lumens formed in segment 150 and handle 40 are formed in a parallel format to simplify mold design.

Of course, material from which sheath 30 and handle 40 is made must be sufficiently rigid to resist bending of segments 102, 152, 154, 156 and 150 and must be sufficiently incompressible to keep tip 90 within segment 150 until needle 70 bends and yet be sufficiently flexible to form pliable hinges 172, 170, 168, 166, 165, 164, 162, 160 and 104. Polypropylene may be used for such purposes. In this manner, a safety catheter insertion needle device can be made from one molded part which comprises all the necessary elements for a handle and a safety guard for rendering the needle safe after use.

The invention disclosed herein may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A safety IV catheter insertion device comprising:
   a handle by which the device is manipulated in the process of inserting an IV catheter into a patient;
   a catheter insertion needle which is securely affixed to said handle, said needle comprising a distally disposed sharpened tip and a hollow bore which communicates with an interior portion of said handle;

a sheath comprising a plurality of foldable parts, at least one of which comprises an orifice disposed about said needle, said sheath being hingeably affixed to said handle on a proximal end and comprising a catheter connecting part disposed about the needle on a distal end;

a catheter disposed about said needle such that said needle tip is exposed for use in catheter insertion, said catheter further being in communication with the catheter connecting part of said sheath;

each of said foldable parts comprising an interconnecting hinge to at least one other foldable part such that the sheath is proximally disposed in a folded state during a medical procedure to provide distal access to the needle and the sharpened tip and then unfolded by manual rotation of one foldable part to extend and slideably displace the catheter from the needle and consequently sandwich the needle between at least two foldable parts thereby forming a substantially rigid structure and covering the needle tip by the catheter connecting part;

a latch associated with said sheath which securely affixes the sheath in relation to the needle such that the sheath and needle combine to form an essentially inconstrictable structure, thereby providing a protective shield which safeguards the needle tip from further access.

2. A safety IV catheter insertion device according to claim 1 wherein said interconnecting hinge comprises a molded living hinge.

3. A safety IV catheter insertion device according to claim 1 wherein said hinge and said foldable parts, in combination, comprise but a single integrally molded part.

4. A safety IV catheter insertion device according to claim 1 wherein said foldable parts and said handle, in combination, comprise but a single integrally molded part.

5. A safety IV catheter insertion device according to claim 1 wherein said handle, said foldable parts and said connector, in combination, comprise but a single integrally molded part.

6. A safety IV catheter insertion device according to claim 1 wherein said handle, said foldable parts, said interconnecting hinges and said connector, in combination, comprise but a single integrally molded part.

7. A method for actuating a safety sheath for a safety I.V. catheter insertion apparatus comprising the steps of:

providing an I.V. catheter insertion needle having a first end whereat a sharpened tip is disposed and a second end whereat the catheter insertion needle is affixed to a needle hub;

providing an I.V. catheter which is disposed about the catheter insertion needle during a catheter insertion process with said sharpened tip extending distally from said catheter during percutaneous entry, said I.V. catheter comprising a proximally disposed medical fluid flow connector;

providing a housing having a surface for gripping and handling said apparatus said housing comprising
an insertion needle hub, distally disposed in said housing, wherein said second end of the catheter insertion needle is securely affixed; and
a foldable and unfoldable safety sheath, comprising a plurality of serially hinged rigid arms with at least one of said arms being disposed about said I.V. catheter needle and, while the apparatus is being used in a needle and catheter insertion process, said arms being folded to a proximally disposed state to permit facile access to the needle and catheter with a most distal arm comprising a fitting which is disposed to be in communicative contact with said medical fluid flow connector;

using the needle, inserting an I.V. catheter into a vessel of a patient;

following I.V. catheter inserting step, rotating one of said arms to thereby unfold said sheath to an unfolded state by rotating at least one of said arms about said needle, whereat the sharp tip is shrouded by the sheath and at least one of said arms is securely latched in the unfolded state whereby said unfolded shroud combines with said needle to form a substantially rigid and inconstrictable structure which safeguards the tip, and concurrently, as a consequence of unfolding said sheath, distally displacing said most distal arm and resultingly displacing the I.V. catheter from said needle as the needle and tip are shrouded by the sheath.

8. A method for actuating a safety sheath for a safety I.V. catheter insertion apparatus according to claim 7 wherein the displacing step comprises continuing to unfold said sheath until at least one click is heard.

9. A method for actuating a safety sheath for a safety I.V. catheter insertion apparatus according to claim 7 wherein the foldable and unfoldable sheath providing step comprises providing a plurality of foldable parts, all of which are displaced to an unfolded state when one part is so displaced.

10. A method for actuating a safety sheath for a safety I.V. catheter insertion apparatus according to claim 9 wherein the unfolding step comprises displacing the one part by a digit of one hand a distance which is less than one-third the length of an unfolded sheath.

11. A catheter insertion needle safety apparatus comprising:

a handle by which an operator inserts a catheter in a medical procedure;

a catheter insertion needle securely affixed to said handle and having a sharpened tip distally disposed relative to said handle;

a catheter disposed about said needle having a having a proximal end securely affixed to a medical fitting;

a sheath hingeably affixed to said handle and comprising a plurality of serially, hingeably interconnected, substantially rigid parts, said parts being disposed in a folded state while said catheter insertion needle is used as a tool for inserting said catheter and being unfoldable by manual rotation of one of the folded parts and comprising at least one latch which affixes the sheath relative to the catheter insertion needle when the sheath is unfolded about the needle; and said sheath further comprising a fitting complementary to said medical fitting, said complementary fitting being disposed about said needle such that unfolding the sheath displaces the catheter along the needle over a linear distance greater than the length of any of the individual rigid parts.

* * * * *